(12) United States Patent
Hughes et al.

(10) Patent No.: US 11,524,980 B2
(45) Date of Patent: Dec. 13, 2022

(54) SYNTHESIS OF ECHINOCANDIN ANTIFUNGAL AGENT

(71) Applicant: Cidara Therapeutics, Inc., San Diego, CA (US)

(72) Inventors: David Hughes, San Diego, CA (US); Martin Patrick Hughes, Spokane, WA (US); Robert Michael Hughes, San Diego, CA (US); Balasingam Radhakrishnan, Chapel Hill, NC (US); Yannick Borguet, Waringstown (GB); Steven McIntyre, Moira (GB)

(73) Assignee: Cidara Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/252,579

(22) PCT Filed: Jun. 14, 2019

(86) PCT No.: PCT/US2019/037176
§ 371 (c)(1),
(2) Date: Dec. 15, 2020

(87) PCT Pub. No.: WO2019/241626
PCT Pub. Date: Dec. 19, 2019

(65) Prior Publication Data
US 2021/0179667 A1 Jun. 17, 2021

Related U.S. Application Data

(60) Provisional application No. 62/685,634, filed on Jun. 15, 2018.

(51) Int. Cl.
*C07K 7/64* (2006.01)

(52) U.S. Cl.
CPC .................................. *C07K 7/64* (2013.01)

(58) Field of Classification Search
None
See application file for complete search history.

(56) References Cited

U.S. PATENT DOCUMENTS

| | | | |
|---|---|---|---|
| 5,965,525 A | 10/1999 | Burkhardt et al. | |
| 8,722,619 B2 | 5/2014 | James, Jr. et al. | |
| 9,006,391 B2 * | 4/2015 | De Pater ................. | C07K 7/56 530/317 |
| 9,217,014 B2 * | 12/2015 | James, Jr. ............... | A61P 7/00 |
| 9,526,835 B2 | 12/2016 | Radhakrishnan et al. | |
| 9,676,821 B2 | 6/2017 | James, Jr. et al. | |
| 10,016,479 B2 | 7/2018 | Radhakrishnan et al. | |
| 10,369,188 B2 | 8/2019 | Bartizal et al. | |
| 10,702,573 B2 | 7/2020 | Radhakrishnan et al. | |
| 10,780,144 B2 | 9/2020 | Bartizal et al. | |
| 2017/0253635 A1 | 9/2017 | James, Jr. et al. | |
| 2018/0256673 A1 | 9/2018 | Balkovec et al. | |
| 2019/0216885 A1 | 7/2019 | Bartizal et al. | |
| 2019/0307843 A1 | 10/2019 | Bartizal et al. | |
| 2019/0374601 A1 | 12/2019 | Bartizal et al. | |
| 2020/0164023 A1 | 5/2020 | Bartizal et al. | |
| 2020/0268833 A1 | 8/2020 | Bartizal et al. | |
| 2021/0002346 A1 | 1/2021 | Bartizal et al. | |
| 2021/0128670 A1 | 5/2021 | Radhakrishnan et al. | |

FOREIGN PATENT DOCUMENTS

| | | |
|---|---|---|
| WO | WO-2012/119065 A2 | 9/2012 |
| WO | WO-2013/142279 A1 | 9/2013 |
| WO | WO-2015/035102 A2 | 3/2015 |
| WO | WO-2016/056022 A2 | 4/2016 |
| WO | WO-2016/201283 A1 | 12/2016 |
| WO | WO-2017/049102 A1 | 3/2017 |
| WO | WO-2017/049105 A1 | 3/2017 |
| WO | WO-2017/120471 A1 | 7/2017 |
| WO | WO-2017/161016 A1 | 9/2017 |
| WO | WO-2018/085200 A1 | 5/2018 |
| WO | WO-2018/102407 A1 | 6/2018 |
| WO | WO-2018/144600 A1 | 8/2018 |
| WO | WO-2018/187574 A1 | 10/2018 |
| WO | WO-2018/191692 A1 | 10/2018 |
| WO | WO-2019/014333 A1 | 1/2019 |
| WO | WO-2019/027498 A1 | 2/2019 |
| WO | WO-2020/086931 A1 | 4/2020 |

OTHER PUBLICATIONS

Khurana et al. (Monatshefte fur Chemie 135, 83-87 (2004)) (Year: 2004).*
International Preliminary Report on Patentability and Written Opinion for International Application No. PCT/US2019/037176, dated Dec. 24, 2020 (8 pages).
International Search Report and Written Opinion for International Application No. PCT/US19/37176, dated Sep. 9, 2019 (14 pages).
Krishnan et al., "CD101, a novel echinocandin with exceptional stability properties and enhanced aqueous solubility," J Antibiot (Tokyo). 70(2):130-135 (2017).
U.S. Appl. No. 17/023,884, filed Sep. 17, 2020 (42 pages).
U.S. Appl. No. 17/029,784, filed Sep. 23, 2020 (75 pages).
U.S. Appl. No. 17/107,627, filed Nov. 30, 2020 (52 pages).
U.S. Appl. No. 17/288,172, filed Apr. 23, 2021 (33 pages).
Leonard Jr. et al., "Synthesis of the antifungal beta-1,3-glucan synthase inhibitor CANCIDAS (*Caspofungin acetate*) from pneumocandin $B_0$," J Org Chem. 72(7):2335-43 (2007).
Extended European Search Report for European Patent Application No. 19818627.2, dated Feb. 21, 2022 (10 pages).

* cited by examiner

*Primary Examiner* — Sergio Coffa
(74) *Attorney, Agent, or Firm* — Clark & Elbing LLP

(57) ABSTRACT

The present invention relates to echinocandin cyclopeptides and to methods for preparing echinocandin cyclopeptides.

23 Claims, No Drawings

SYNTHESIS OF ECHINOCANDIN ANTIFUNGAL AGENT

BACKGROUND

This invention features methods for the synthesis of compounds useful for treatment of fungal infections and conditions related thereto.

Fungal infections, such as those caused by *Candida* and *Aspergillus*, can be serious and life-threatening infections that represent a significant public health issue, particularly in highly vulnerable populations including the elderly, post-surgical, critically ill, and other hospitalized patients with serious medical conditions. Because of increasing resistance to existing antifungal drugs, there is an urgent need to develop new and more effective antifungal agents to treat these serious infections. Echinocandins are members of a leading class of antifungal agents for the treatment of fungal infections. These compounds target the cell wall by preventing the production of 1,3-β-D-glucan through inhibition of the catalytic subunit of 1,3-β-D-glucan synthase enzyme complex.

Although nature can provide a substantive part of the complex chemical structure of semisynthetic cyclopeptides, and in many cases having all chiral centers in the required configuration, the subsequent chemical conversions into the therapeutically active derivatives nevertheless often require unprecedented approaches. Usually the structures in question are chemically unstable and/or prone to racemization and simply do not allow for otherwise obvious synthetic manipulation taught in synthetic organic chemical textbooks. This chemical instability is even more pronounced in anidulafungin, caspofungin, and micafungin due to the presence of the notoriously fragile hemiaminal or aminal moieties. The production of pharmaceutical grade echinocandins is complicated by the difficulty and expense of relying upon chromatographic methods to remove structurally similar impurities produced in the course of the commercial scale production of these antifungal agents.

There is a need for convenient synthetic alternatives that permit the commercial scale production of semisynthetic echinocandins. These approaches can be useful alternatives to existing synthetic methods and can achieve a higher yield, higher isomeric purity, elimination of a mutagenic impurity, a reduced waste stream, or any combination of the above.

SUMMARY OF THE INVENTION

The invention features a method of synthesizing compound 1, the method including the steps of: (a) providing a first composition including a boronate ester of anidulafungin; (b) providing a second composition including a salt of choline; (c) combining the first composition, the second composition, and an acid to form a mixture, wherein the solvent system is selected to form a precipitate of a reaction product having formula (I):

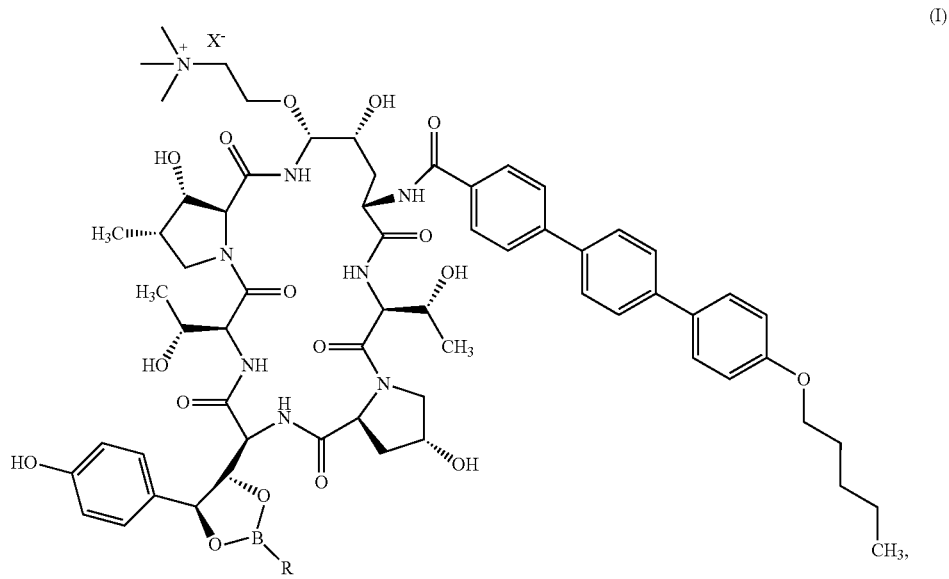

(I)

where $X^-$ is an anion; and R is $C_1$-$C_6$ alkyl, $C_3$-$C_{10}$ carbocyclyl, $C_2$-$C_6$ alkenyl, $C_6$-$C_{10}$ aryl, or $C_2$-$C_9$ heteroaryl; and (d) hydrolyzing the compound of formula (I) to form compound 1, or a salt or neutral form thereof.

In some embodiments, R is $C_1$-$C_6$ alkyl or $C_6$-$C_{10}$ aryl. In some embodiments, R is $C_6$-$C_{10}$ aryl. In some embodiments, R is substituted or unsubstituted $C_6$ aryl.

In some embodiments, the concentration of the mixture is at least 0.01, 0.02, 0.03, 0.04, 0.05, 0.06, 0.07, 0.08, 0.09, or 0.1 moles per L (e.g., from 0.01 to 0.03 moles per L, from 0.03 to 0.05 moles per L, from 0.05 to 0.1 moles per L, or from 0.1 to 0.2 moles per L) relative to the compound of formula (I). In some embodiments, the concentration of the mixture is at least 0.1, 0.15, 0.2, 0.25, 0.3, 0.35, 0.4, 0.45, or 0.5 moles per L (e.g., from 0.1 to 0.3 moles per L, from 0.2 to 0.4 moles per L, from 0.3 to 0.5 moles per L, from 0.4 to 0.6 moles per L, or from 0.5 to 0.7 moles per L) relative to the compound of formula (I). In some embodiments, the concentration of the mixture is at least 0.5, 0.6, 0.7, 0.8, 0.9, or 1.0 moles per L (e.g., from 0.5 to 0.8 moles per L, from 0.6 to 0.9 moles per L, from 0.7 to 1.0 moles per L, from 1.0 to 1.3 moles per L, from 1.0 to 1.5 moles per L, or from 1.5 to 2.0 moles per L) relative to the compound of formula (I).

In some embodiments, step (c) includes a solvent system that includes acetonitrile, tetrahydrofuran, 2-methyltetrahydrofuran, 1,2-dimethoxyethane, cyclopentylmethyl ether, or tert-butyl methyl ether, or mixtures thereof. In some embodiments, step (c) includes a solvent system that includes a mixture of tetrahydrofuran and acetonitrile. In some embodiments, step (c) includes a solvent system that includes a mixture of 2-methyltetrahydrofuran and acetonitrile. Optionally, the solvent system further includes trifluoroacetic anhydride. In some embodiments, the solvent system contains from 0.1% to 5% (w/w) water. In some embodiments, the solvent system is anhydrous.

In some embodiments, step (c) includes combining at least 10, 15, 20, 25, 30, 35, or 40 molar equivalents (e.g., from 10 to 80, from 10 to 40, from 20 to 60, or from 20 to 40 equivalents) of the salt of choline and at least 1 molar equivalent of anidulafungin, as its boronate ester.

In particular embodiments, step (c) is performed at a temperature of less than 40° C., 35° C., 30° C., 25° C., 20° C., 18° C., 15° C., 12° C., or 10° C. (e.g., from 2 to 40° C., from 5 to 40° C., from 8 to 20° C., from 8 to 18° C., or from 8 to 12° C.).

In some embodiments, step (c) includes the step of forming a mixture in which at least 50%, 60%, 70%, 80%, 90%, or 95% (e.g., from 50-55%, from 55-60%, from 60-65%, from 65-70%, from 70-75%, from 75-80%, from 80-85%, from 85-90%, from 90-95%, from 95-99%, or from 98-99%) of the compound of formula (I) relative to the final amount of the compound of formula (I) produced is precipitated.

In some embodiments, step (c) includes the precipitation of at least 50%, 60%, 70%, 80%, 90%, or 95% (e.g., from 50-55%, from 55-60%, from 60-65%, from 65-70%, from 70-75%, from 75-80%, from 80-85%, from 85-90%, from 90-95%, from 95-99%, or from 98-99%) of the compound of formula (I) relative to the final amount of the compound of formula (I) produced.

In some embodiments, the second composition can include a solution of the salt of choline dissolved in a mixture of acetonitrile and trifluoroacetic acid (TFA), optionally with one or more additional organic acids. For example, the additional organic acid that may be used in combination with acetonitrile and TFA can be methanesulfonic acid or acetic acid. In some embodiments, the second composition can include a solution of the salt of choline dissolved in a mixture of acetonitrile and acetic acid. In some embodiments, the second composition can include a solution of the salt of choline dissolved in a mixture of acetonitrile and methanesulfonic acid. In some embodiments, the second composition can include a solution of the salt of choline dissolved in a mixture of acetonitrile and trifluoromethanesulfonic acid. In particular embodiments, the second composition further includes trifluoroacetic anhydride. In some embodiments, the second composition contains from 0.1% to 5% (w/w) water. In some embodiments, the second composition is an anhydrous solution, or the second composition is a mixture comprising one or more anhydrous solvents.

This invention features a method of synthesizing compound 1, the method including the steps of: (a) providing a first composition including an arylboronate ester of anidulafungin; (b) providing a second composition including a salt of choline; (c) combining the first composition, the second composition, and an acid to form a mixture including a compound of formula (II):

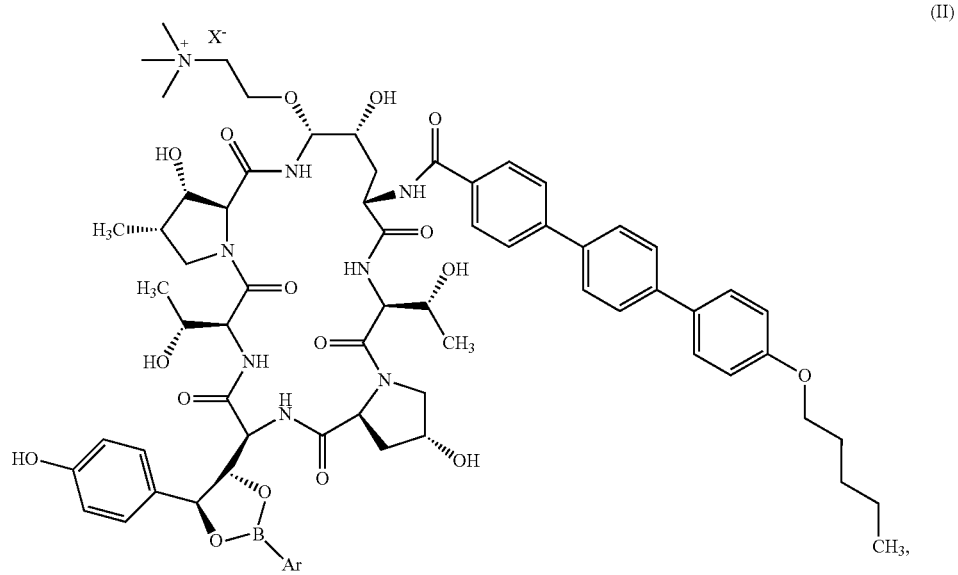

where $X^-$ is an anion; and Ar is substituted or unsubstituted $C_6$ aryl; and (d) hydrolyzing the compound of formula (II) to form compound 1, or a salt or neutral form thereof.

In some embodiments, Ar is phenyl, 3,4-dimethoxyphenyl, 4-trifluoromethylphenyl, or 2,6-dimethylphenyl. In some embodiments, Ar is phenyl. In some embodiments, Ar is 3,4-dimethoxyphenyl. In other embodiments, Ar is 4-trifluoromethylphenyl. In still other embodiments, Ar is 2,6-dimethylphenyl.

In certain embodiments of the method, step (c) includes combining at least 10, 15, 20, 25, 30, 35, or 40 molar equivalents (e.g., from 10 to 80, from 10 to 40, from 20 to 60, or from 20 to 40 equivalents) of the salt of choline with 1 molar equivalent of the 3,4-dimethoxyphenylboronate ester of anidulafungin. In certain embodiments of the method, step (c) includes combining at least 10, 15, 20, 25, 30, 35, or 40 molar equivalents (e.g., from 10 to 80, from 10 to 40, from 20 to 60, or from 20 to 40 equivalents) of the salt of choline with 1 molar equivalent of the 4-trifluoromethylphenylboronate ester of anidulafungin. In certain embodiments of the method, step (c) includes combining at least 10, 15, 20, 25, 30, 35, or 40 molar equivalents (e.g., from 10 to 80, from 10 to 40, from 20 to 60, or from 20 to 40 equivalents) of the salt of choline with 1 molar equivalent of the 2,6-dimethylphenylboronate ester of anidulafungin.

In some embodiments, the first composition includes a solution of the 3,4-dimethoxyphenylboronate ester of anidulafungin dissolved in an organic solvent selected from acetonitrile, tetrahydrofuran, 2-methyltetrahydrofuran, 1,2-dimethoxyethane, cyclopentylmethyl ether, tert-butyl methyl ether, or mixtures thereof. In some embodiments, the first composition includes a solution of the 4-trifluoromethylphenylboronate ester of anidulafungin dissolved in an organic solvent selected from acetonitrile, butyronitrile, tetrahydrofuran, 2-methyltetrahydrofuran, 1,2-dimethoxyethane, cyclopentylmethyl ether, tert-butyl methyl ether or mixtures thereof. In some embodiments, the first composition includes a solution of the 2,6-dimethylphenylboronate ester of anidulafungin dissolved in an organic solvent selected from acetonitrile, butyronitrile, tetrahydrofuran, 2-methyltetrahydrofuran, 1,2-dimethoxyethane, cyclopentylmethyl ether, tert-butyl methyl ether or mixtures thereof. In some embodiments, the organic solvent contains from 0.1% to 5% (w/w) water. In some embodiments, the organic solvent is anhydrous.

In some embodiments, the second composition can include a solution of the salt of choline dissolved in a mixture of acetonitrile and trifluoroacetic acid (TFA). In particular embodiments, the second composition includes a solution of the salt of choline dissolved in a mixture of acetonitrile, trifluoroacetic acid, and trifluoroacetic anhydride. The second composition can include a solution of the salt of choline dissolved in a mixture of acetonitrile and acetic acid. In particular embodiments, the second composition includes a solution of the salt of choline dissolved in a mixture of acetonitrile, trifluoroacetic acid, and acetic acid. The second composition can include a solution of the salt of choline dissolved in a mixture of acetonitrile and methanesulfonic acid.

The second composition can include a solution of the salt of choline dissolved in a mixture of acetonitrile and trifluoromethanesulfonic acid. In particular embodiments, the second composition further includes trifluoroacetic anhydride. In some embodiments, the second composition contains from 0.1% to 5% (w/w) water. In some embodiments, the second composition is anhydrous, or the second composition is a mixture of one or more anhydrous solvents.

In a particular embodiment of any of the above methods, step (c) further includes the step of adding acetonitrile to the mixture to reduce the level of compound 1 beta-diastereomer.

In some embodiments of any of the above methods the mixture is formed at a temperature of less than 40° C., 35° C., 30° C., 25° C., 20° C., 18° C., 15° C., 12° C., or 10° C. (e.g., from 2 to 40° C., from 5 to 40° C., from 8 to 20° C., from 8 to 18° C., or from 8 to 12° C.).

In some embodiments, step (c) further comprises diluting with at least 5, 6, 7, 8, 9, or 10 volumes relative to anidulafungin of water or a mixture of water with acetonitrile. In some embodiments, step (c) further comprises diluting with at least 10, 11, 12, 13, 14, or 15 volumes relative to anidulafungin of water or a mixture of water with acetonitrile. In some embodiments, step (c) further comprises diluting with at least 15, 20, 25, 30, 35, 40, 45, or 50 volumes relative to anidulafungin of water or a mixture of water with acetonitrile.

In some embodiments, the mixture of water with acetonitrile includes at least 5%, 10%, 15%, 20%, 25%, or 30% water. In some embodiments, the mixture of water with acetonitrile includes at least 30%, 35%, 40%, 45%, or 50% water. In some embodiments, the mixture of water with acetonitrile includes at least 50%, 55%, 60%, 65%, or 70% water. In some embodiments, the mixture of water with acetonitrile includes at least 70%, 75%, 80%, 85%, 90%, or 95% water.

In some embodiments, step (d) further comprises addition of base to adjust the pH to at least 2 (e.g., from 2 to 3, from 2 to 4, or from 2 to 5). In particular embodiments, step (d) includes diluting with at least 5 volumes relative to anidulafungin of water:acetonitrile mixture of about 80:20 to 50:50 and adjusting the pH with base to a pH of from 2 to 5.

In some embodiments, the base is ammonium acetate, ammonium hydroxide, or ammonium carbonate. In some embodiments, the base is ammonium acetate. In some embodiments, the base is ammonium hydroxide. In some embodiments, the base is ammonium carbonate.

In a particular embodiment of any of the above methods, step (d) includes forming a reaction product including greater than 70%, 75%, 80%, 85%, 88%, or 90% (e.g., from 70% to 95%, from 75% to 90%, from 80% to 90%, or from 85% to 90%) compound 1 (as measured by HPLC) and less than 5%, 4%, 3.5%, 3.0%, 2.5%, 2.0%, 1.5% or 1.0% (e.g., from 0% to 1%, from 0% to 2%, from 0% to 3%, from 1.0% to 4.0%, from 1.0% to 3.0%, from 1.5% to 3.5%, or from 2.0% to 3.0%) compound 1 beta-diastereomer (as measured by HPLC). For example, step (d) can include forming a reaction product including greater than 75% compound 1 (as measured by HPLC), less than 2% compound 1 beta-diastereomer (as measured by HPLC), and, optionally, less than 1% (e.g., from 0% to 0.5%, from 0.5% to 1.0% or from 0.7% to 1.0%) compound 1 epimer (as measured by HPLC). In some embodiments, step (d) includes forming a reaction product including from 75% to 90% compound 1 (as measured by HPLC) and from 1.5% to 3.5% compound 1 beta-diastereomer (as measured by HPLC). In some embodiments, step (d) includes forming a reaction product including from 75% to 90% compound 1 and from 0.5% to 2.5% compound 1 beta-diastereomer. In other embodiments, step (d) includes forming a reaction product including from 75% to 90% compound 1 (as measured by HPLC), from 1.5% to 3.5% compound 1 beta-diastereomer (as measured by HPLC), and from 0.5% to 1.0% compound 1 epimer (as measured by HPLC). In other embodiments, step (d) includes forming a reaction product including from 75% to 90% compound 1, from 0.5% to 2.5% compound 1 beta-diastereomer, and from 0.1% to 1.0% compound 1 epimer. In a related aspect, the invention features a method of synthesizing compound 1, the method including: hydrolyzing a compound of formula (IIa):

neutral form thereof, compound 1, or a salt or neutral form thereof, can be separated from 3,4-dimethoxyphenylboronic acid by passage across an ion exchange column or by preparative HPLC.

In any of the above methods, after hydrolyzing the compound of formula (IIb) to form compound 1, or a salt or neutral form thereof, compound 1, or a salt or neutral form thereof, can be separated from 4-trifluoromethylphenylboronic acid by passage across an ion exchange column or by preparative HPLC.

In any of the above methods, after hydrolyzing the compound of formula (IIc) to form compound 1, or a salt or neutral form thereof, compound 1, or a salt or neutral form

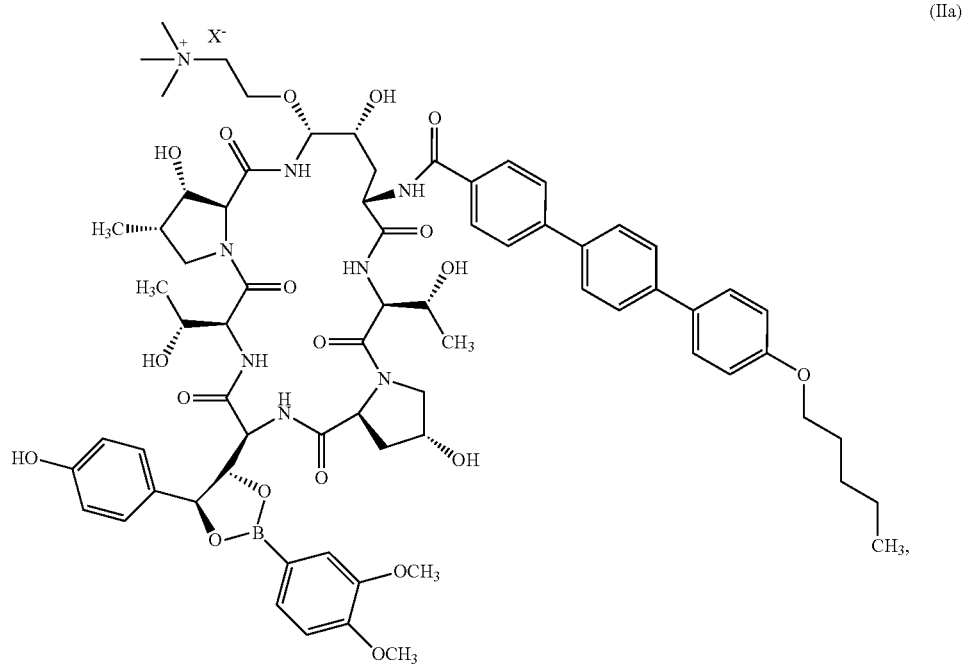

(IIa)

wherein $X^-$ is an anion, to form compound 1, or a salt or neutral form thereof.

In any of the above methods, the hydrolyzing can include contacting the compound of any one of formulas (I), (II), (IIa), (IIb), or (IIc) with a base.

In some embodiments, the base is an aqueous base. In particular embodiments, the hydrolyzing is performed at a temperature of less than 15° C., 12° C., 10° C., or 8° C. (e.g., from 2 to 15° C., from 5 to 15° C., from 5 to 12° C., from 5 to 10° C., or from 2 to 10° C.).

In particular embodiments, the hydrolyzing comprises diluting with at least 5 volumes relative to anidulafungin of water:acetonitrile mixture of about 80:20 to 50:50 and adjusting the pH with base to a pH of from 2 to 5.

In any of the above methods, after hydrolyzing the compound of formula (IIa) to form compound 1, or a salt or thereof, can be separated from 2,6-dimethylphenylboronic acid by passage across an ion exchange column or by preparative HPLC.

In other embodiments, hydrolyzing to form compound 1 is performed on a scale that produces from 100 grams to 50 Kg of compound 1 (e.g., 100-200 grams, 200-500 grams, 500-1000 grams, 1-5 kg, 5-10 kg, 10-20 kg, 20-40 kg, or 30-50 kg).

In any of the above methods, the method can further include producing a pharmaceutical composition by combining the compound 1, or a salt or neutral form thereof, with pharmaceutically acceptable excipients (e.g., any excipient described herein). For example, the pharmaceutical composition can be formulated for topical or parenteral administration, or any form of administration described herein.

In a related aspect, the invention features a compound of formula (IIa):
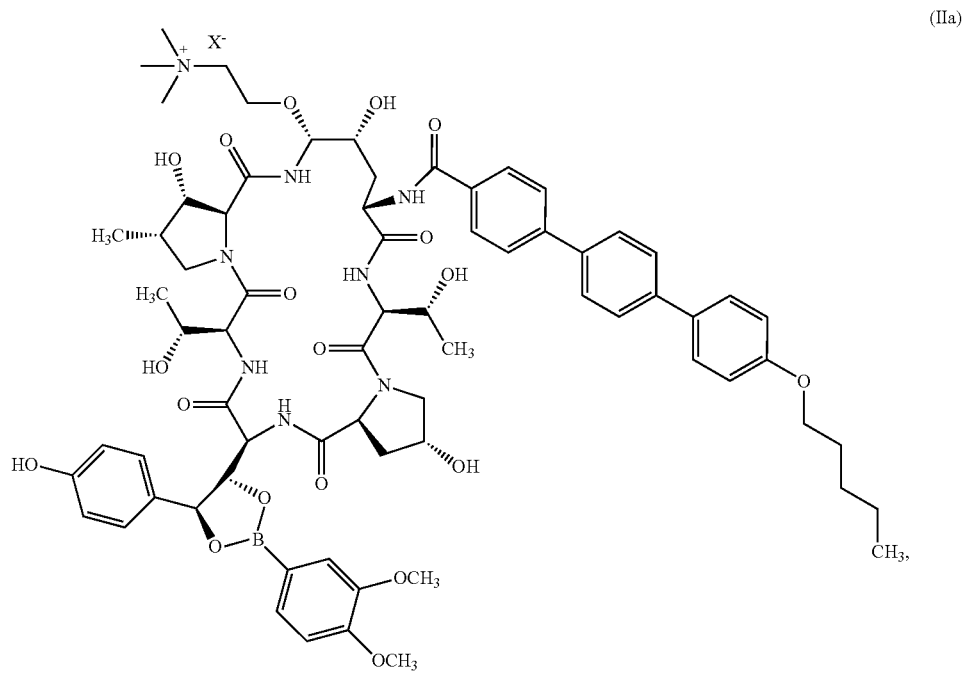
(IIa)
where X⁻ is an anion.
In another aspect, the invention features a compound of formula (IIb):
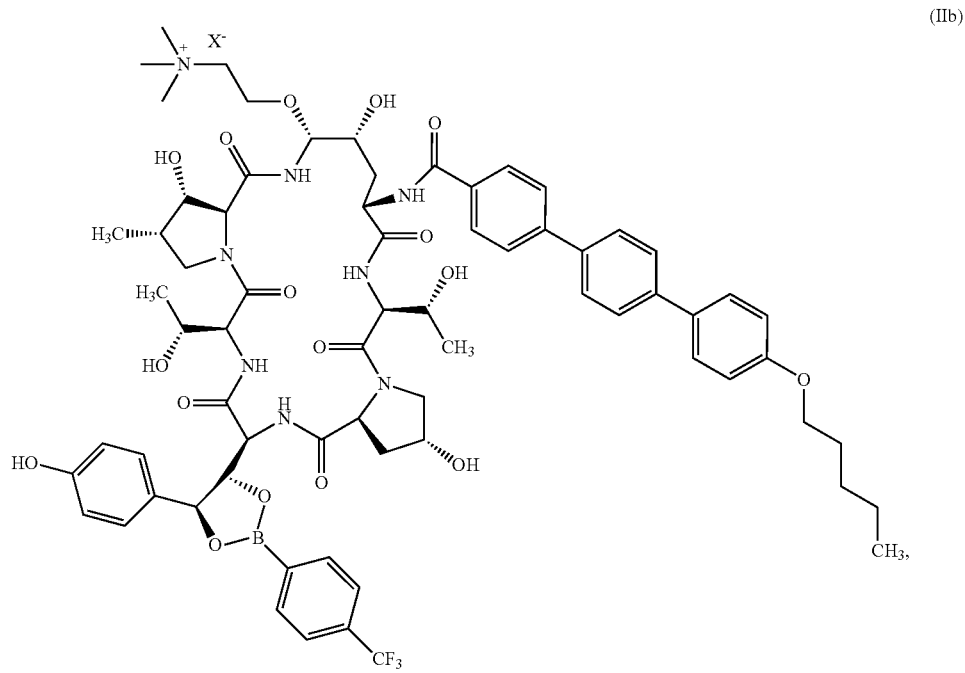
(IIb)
where X⁻ is an anion.

In yet another aspect, the invention features a compound of formula (IIc):

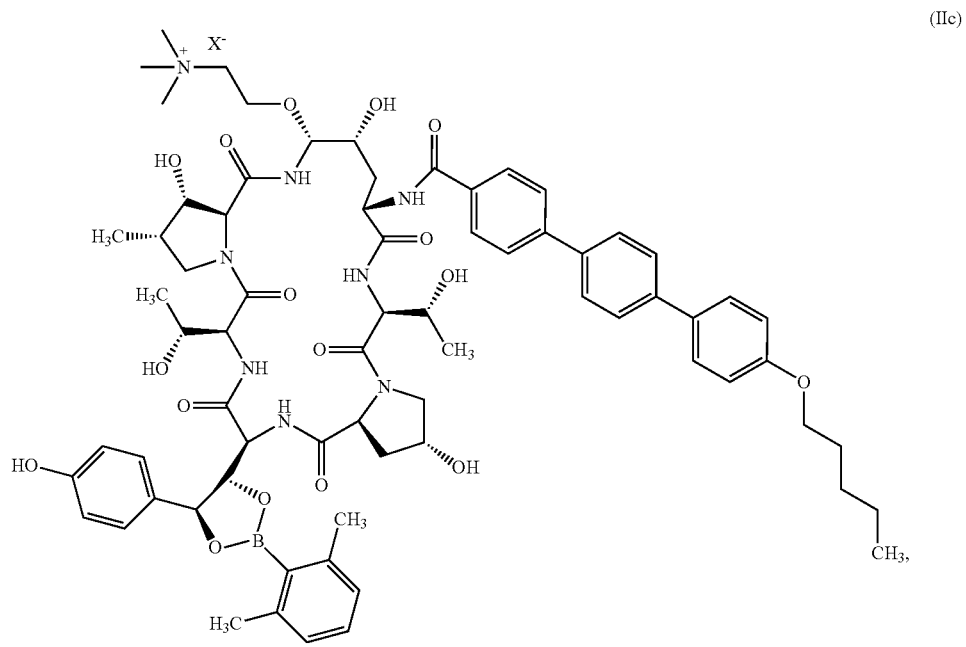

where X⁻ is an anion.

In another aspect, the invention features a pharmaceutical composition including compound 1, or a salt or neutral form thereof, and a pharmaceutically acceptable excipient, wherein the pharmaceutical composition comprises less than 5%, 4%, 3.5%, 3.0%, 2.5%, 2.0%, 1.5% or 1.0% (e.g., from 0% to 2.0%, from 0.1% to 4.0%, from 0.75% to 3.0%, from 0.5% to 3.5%, or from 1.0% to 3.0%) (w/w) compound 1 beta-diastereomer. In particular embodiments, the pharmaceutical composition also includes less than 1% (e.g., from 0.5% to 1.0% or from 0.7% to 1.0%) (w/w) compound 1 epimer relative to the weight of compound 1, or a salt or neutral form thereof, in the pharmaceutical composition. In some embodiments, the pharmaceutical composition includes from 1.5% to 3.5% (w/w) compound 1 beta-diastereomer and from 0.5% to 1.0% (w/w) compound 1 epimer relative to the weight of compound 1, or a salt or neutral form thereof, in the pharmaceutical composition.

Definitions

As used herein, the term "anhydrous solvent system" or "solvent system is anhydrous" refers to a solvent system that is dried prior to use in the reaction and/or that contains less than 0.1% of water. For example, "anhydrous acetonitrile" or "acetonitrile is anhydrous" refers to acetonitrile that is dried prior to use in the reaction and/or acetonitrile that contains less than 0.1% of water.

As used herein, the term "compound 1" refers to the compound having the structure shown below. The term "compound 1 in salt form" or "a salt of compound 1" refers to compound 1 when its tertiary ammonium ion positive charge is balanced with a negative counterion (e.g., an acetate).

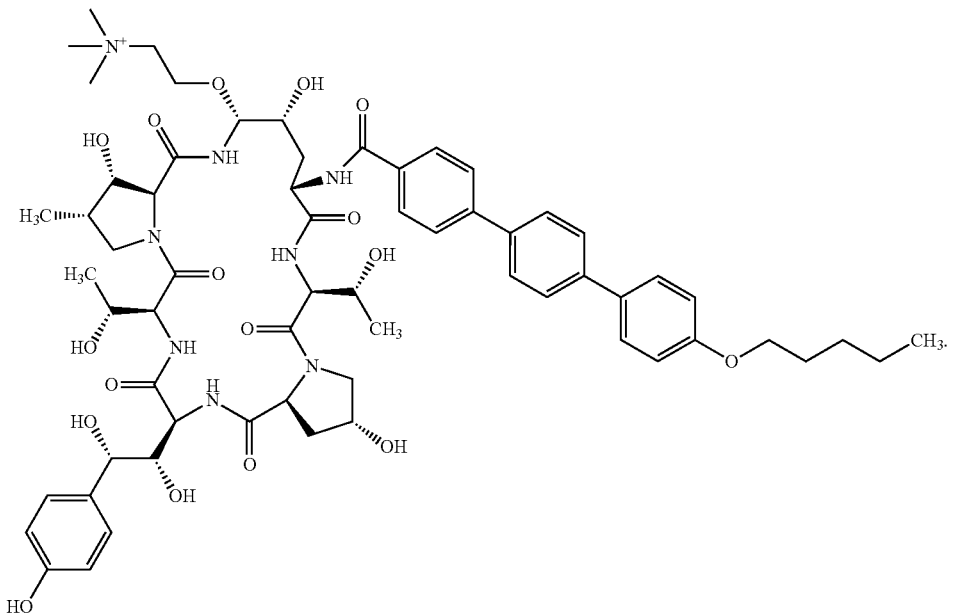

(compound 1)

As used herein, the term "a neutral form" includes zwitterionic forms of compound 1 in which compound 1 has no net positive or negative charge. The zwitterion is present in a higher proportion in basic medium (e.g., pH of between 7 and 8, between 8 and 9, or between 9 and 10) relative to compound 1 or a salt of compound 1. In some embodiments, the zwitterion may also be present in its salt form.

As used herein, the term "compound 1 beta-diastereomer" or "beta-diastereomer" refers to the compound having the structure shown below, and salts thereof.

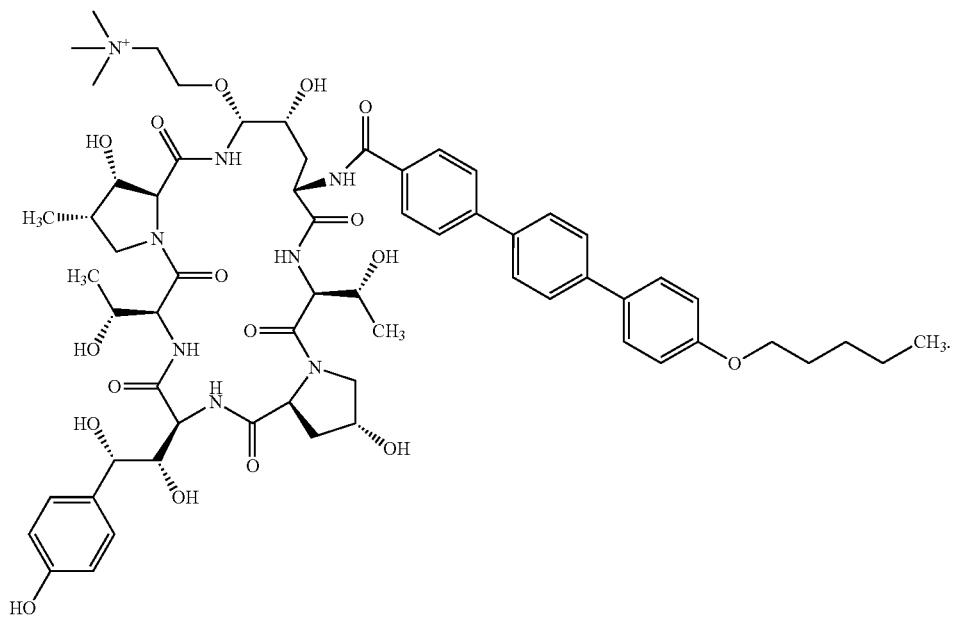

(compound 1 beta-diastereomer)

As used herein, the term "compound 1 epimer" or "epimer" refers to the compound having the structure shown below, and salts thereof.

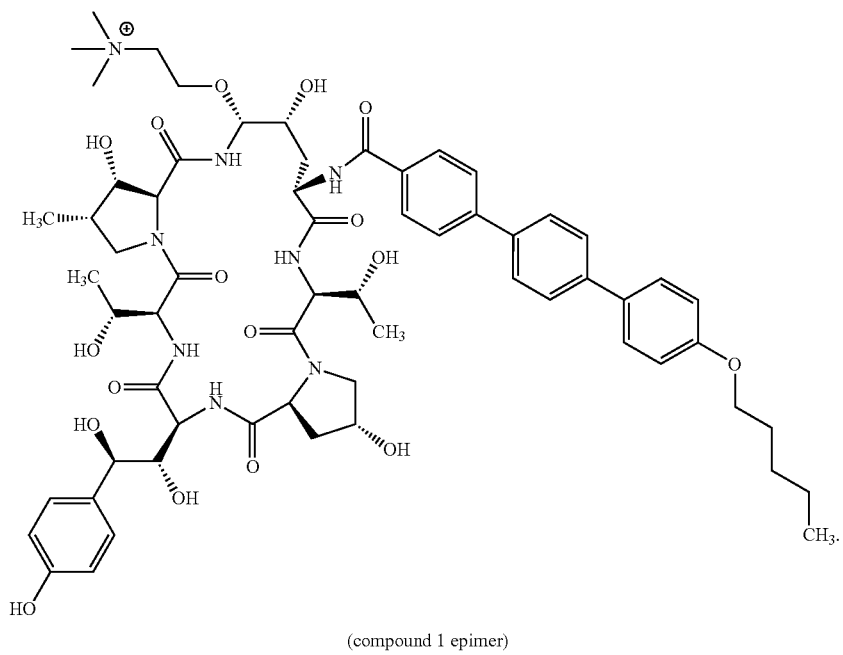 [SMILES: CCCCCOc1ccc(-c2ccc(-c3ccc(C(=O)N[C@H]4C[C@@H](O)[C@@H](OCC[N+](C)(C)C)NC(=O)[C@@H]5[C@@H](O)[C@@H](C)CN5C(=O)[C@H]([C@@H](C)O)NC(=O)[C@H]([C@H](O)[C@H](O)c5ccc(O)cc5)NC(=O)[C@@H]5C[C@@H](O)CN5C(=O)[C@H]([C@@H](C)O)NC4=O)cc3)cc2)cc1]

(compound 1 epimer)

As used herein, the term "arylboronate ester of anidulafungin" refers to the compound having the structure shown below, and salts thereof.

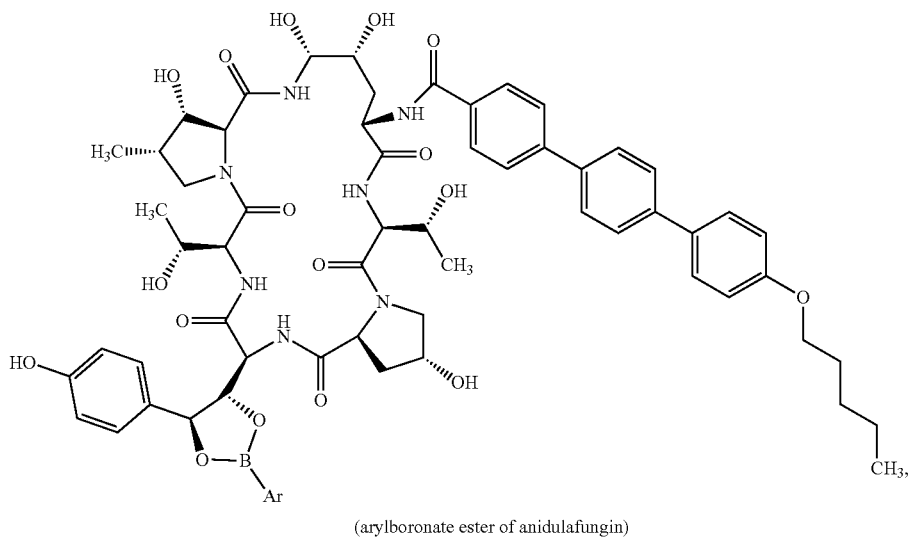

(arylboronate ester of anidulafungin)

where Ar is a substituted or unsubstituted $C_6$ aryl group.

As used herein, the term "echinocandin-containing" refers to compound 1, compound 1 beta-diastereomer, and/or compound 1 epimer. For example, "echinocandin-containing reaction product" may refer to a reaction product that includes compound 1, compound 1 beta-diastereomer, and/or compound 1 epimer.

As used herein, the term "about" refers to a range of values that is ±10% of specific value. For example, "about 150 mg" includes ±10% of 150 mg, or from 135 mg to 165 mg. Such a range performs the desired function or achieves the desired result. For example, "about" may refer to an amount that is within less than 10% of, within less than 5% of, within less than 1% of, within less than 0.1% of, and within less than 0.01% of the stated amount.

As used herein, the term "between" refers to any quantity within the range indicated and enclosing each of the ends of the range indicated. For example, a pH of between 5 and 7 refers to any quantity within 5 and 7, as well as a pH of 5 and a pH of 7.

As used herein, the term "infection" or "fungal infection" is meant a microbial dysbiosis characterized by overgrowth or colonization of any part of the body of a human subject by one or more species of fungi (e.g., fungal pathogens or opportunistic pathogens), reduction of which may provide benefit to the host. For example, the infection may include the excessive growth of or colonization by fungal species that are normally present in or on the body of a human subject, or the infection may include colonization by fungal species that are not normally present in or on the body of a human subject. In some instances, the infection may include colonization of a part of the body by a fungus that is indigenous to some parts of the human body (e.g., GI tract) but is detrimental when found in other parts of the body (e.g., tissues beyond the GI tract). More generally, an infection can be any situation in which the presence of a microbial population(s) is damaging to a host body.

As used herein, the term "$C_6$ aryl" refers to an aromatic radical of 6 carbon atoms that is unsubstituted or substituted. Substitutions can include halogen, methyl, ethyl, ethoxy, methoxy, fluoromethyl, difluoromethyl, and trifluoromethyl. $C_6$ aryl groups include, without limitation, phenyl, 3,4-dimethoxyphenyl, 4-trifluoromethylphenyl, and 2,6-dimethylphenyl. In some embodiments, a $C_6$ aryl group is substituted with one, two, three, four, or five substituents independently selected from the group consisting of: (1) halo; (2) $C_1$-$C_6$ alkoxy; (3) $C_1$-$C_6$ alkyl (e.g., $C_1$-$C_6$ perfluoroalkyl); and (4) $C_6$-$C_{10}$ aryl. In some embodiments, each of these groups can be further substituted as described herein.

As used herein, the term "salt" refers to any salt form commonly used in the pharmaceutical industry. Acid addition salts include organic acids, such as acetic, formic, lactic, palmoic, maleic, citric, cholic acid, capric acid, caprylic acid, lauric acid, glutaric, glucuronic, glyceric, glycocolic, glyoxylic, isocitric, isovaleric, lactic, malic, oxalo acetic, oxalosuccinic, propionic, pyruvic, ascorbic, succinic, benzoic, palmitic, suberic, salicylic, tartaric, methanesulfonic, toluenesulfonic, and trifluoroacetic acids, and inorganic acids, such as hydrochloric acid, hydrobromic acid, sulfuric acid, and phosphoric acid. Representative alkali or alkaline earth metal salts include sodium, lithium, potassium, calcium, and magnesium, among others.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substitutes are disclosed in groups or in ranges, unless otherwise indicated, the present disclosure is intended to cover individual compounds and groups of compounds (e.g., genera and subgenera) containing each and every individual subcombination of members at each position.

The term "alkyl," as used herein, refers to saturated hydrocarbon groups containing from 1 to 20 (e.g., from 1 to 10 or from 1 to 6) carbons. In some embodiments, an alkyl group is unbranched (i.e., is linear); in some embodiments, an alkyl group is branched. Examples of alkyl groups include, but are not limited to, methyl, ethyl, n- and iso-propyl, n-, sec-, iso- and tert-butyl, and neopentyl. In some embodiments, an alkyl group is unsubstituted. In some embodiments, an alkyl group is substituted with one, two, three, four, or five substituents independently selected from the group consisting of: (1) halo; (2) $C_1$-$C_6$ alkoxy; (3) $C_1$-$C_6$ perfluoroalkyl; and (4) $C_6$-$C_{10}$ aryl. In some embodiments, each of these groups can be further substituted as described herein.

The term "alkenyl," as used herein, represents monovalent straight or branched chain groups of, unless otherwise specified, from 2 to 10 carbons (e.g., from 2 to 4 or from 2 to 6 carbons) containing one or more carbon-carbon double bonds. Examples of alkenyl groups include, but are not limited to, ethenyl, 1-propenyl, 2-propenyl, 2-methyl-1-propenyl, 1-butenyl, and 2-butenyl. In some embodiments, an alkenyl group is unsubstituted. In some embodiments, an alkenyl group is substituted with one, two, three, four, or five substituents independently selected from the group consisting of: (1) halo; (2) $C_1$-$C_6$ alkoxy; (3) $C_1$-$C_6$ alkyl (e.g., $C_1$-$C_6$ perfluoroalkyl); and (4) $C_6$-$C_{10}$ aryl. In some embodiments, each of these groups can be further substituted as described herein.

The term "aryl," as used herein, represents a mono-, bicyclic, or multicyclic carbocyclic ring system having one or two aromatic rings. Examples of aryl groups include, but are not limited to, phenyl, naphthyl, 1,2-dihydronaphthyl, 1,2,3,4-tetrahydronaphthyl, anthracenyl, phenanthrenyl, fluorenyl, indanyl, and indenyl. In some embodiments, an aryl group is unsubstituted. In some embodiments, an aryl group is substituted with one, two, three, four, or five substituents independently selected from the group consisting of: (1) halo; (2) $C_1$-$C_6$ alkoxy; (3) $C_1$-$C_6$ alkyl (e.g., $C_1$-$C_6$ perfluoroalkyl); and (4) $C_6$-$C_{10}$ aryl. In some embodiments, each of these groups can be further substituted as described herein. Examples of substitutions include, but are not limited to, halo, methyl, ethyl, ethoxy, methoxy, fluoromethyl, difluoromethyl, and trifluoromethyl.

The term "carbocyclyl," as used herein, refers to represent monocyclic, bicyclic, or tricyclic non-aromatic ring structure in which the rings are formed by carbon atoms. Examples of carbocyclyl groups include, but are not limited to, cycloalkyl and cycloalkenyl. In some embodiments, a carbocyclyl group is unsubstituted. In some embodiments, a carbocyclyl group is substituted with one, two, three, four, or five substituents independently selected from the group consisting of: (1) halo; (2) $C_1$-$C_6$ alkoxy; (3) $C_1$-$C_6$ alkyl (e.g., $C_1$-$C_6$ perfluoroalkyl); and (4) $C_6$-$C_{10}$ aryl. In some embodiments, each of these groups can be further substituted as described herein.

The terms "halo" or "halogen," as used herein, refer to a fluorine (fluoro), chlorine (chloro), bromine (bromo), or iodine (iodo) radical.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiments, a heteroaryl group is unsubstituted. In some embodiments, a heteroaryl group is substituted with one, two, three, four, or five substituents independently selected from the group consisting of: (1) halo; (2) $C_1$-$C_6$ alkoxy; (3) $C_1$-$C_6$ alkyl (e.g., $C_1$-$C_6$ perfluoroalkyl); and (4) $C_6$-$C_{10}$ aryl. In some embodiments, each of these groups can be further substituted as described herein.

The term "heterocyclyl," as used herein, represents a 5-, 6- or 7-membered ring, unless otherwise specified, containing one, two, three, or four heteroatoms independently selected from the group consisting of nitrogen, oxygen, and sulfur. In some embodiments, a heterocyclyl group is unsubstituted. In some embodiments, a heterocyclyl group is substituted with one, two, three, four, or five substituents independently selected from the group consisting of: (1) halo; (2) $C_1$-$C_6$ alkoxy; (3) $C_1$-$C_6$ alkyl (e.g., $C_1$-$C_6$ perfluoroalkyl); and (4) $C_6$-$C_{10}$ aryl. In some embodiments, each of these groups can be further substituted as described herein.

Other features and advantages of the invention will be apparent from the following detailed description and the claims.

DETAILED DESCRIPTION

Provided herein are synthetic methods and intermediates for making the echinocandin antifungal agent compound 1, or a salt or neutral form thereof. The methods and intermediates can be useful for achieving a higher yield, a higher chemical purity, and/or a higher diastereomeric purity, and a lower cost for the preparation of compound 1. Further synthetic details are provided in the Examples.

The invention features a process for synthesis of compound 1 acetate from anidulafungin using aryl boronic acids as an in situ protecting group, which was developed as follows. In one embodiment, the first step involves slurrying of choline chloride in 2-methyltetrahydrofuran, which is then distilled off. The resulting solid is further dried in a vacuum oven at elevated temperature. The second step involves protecting the anidulafungin starting material by converting it into its 3,4-dimethoxyphenylboronate ester by reacting with 1.3 equivalents of 3,4-dimethoxyphenylboronic acid in tetrahydrofuran. Evaporation of the solvent under reduced vacuum affords the protected intermediate as a solid which is further dried by repeated azeodrying cycles with 2-methyltetrahydrofuran. Alternatively, other methods of water removal can be employed, such as addition of activated molecular sieves, continuous distillation, or addition of dehydrating agents. In the third and final step to the crude material, the azeodried choline chloride is dissolved in a mixture of TFA and acetonitrile and conjugated to the protected anidulafungin backbone to afford the compound 1 as its TFA/chloride form. The reaction is then quenched by addition of a water:acetonitrile mixture and the pH is adjusted to afford a reasonably stable crude mixture that is ready to be fed into the purification process.

The invention features a process for the synthesis of compound 1 acetate from anidulafungin, which entails using 3,4-dimethoxyphenyl boronic acid as an in situ protecting group, wherein, when the conjugation reaction is complete, additional acetonitrile (20 to 50 volumes relative to anidulafungin) is added. This causes precipitation of compound 1. Since the equilibrium between compound 1 and the beta-isomer of 1 (approximately 95:5) in solution is maintained under the acidic conditions, the precipitation of compound 1 from solution results in driving formation of compound 1 and lowering the beta-isomer amount. The beta isomer at the end of reaction can be controlled to no more than 2.0% under these conditions.

The invention features a process for the synthesis of compound 1 acetate from anidulafungin using 3,4-dimethoxyphenyl boronic acid as an in situ protecting group involves conducting the conjugation reaction with 12-18 equivalents of choline chloride under more concentrated conditions. This causes precipitation of compound 1 as the reaction proceeds. Since the equilibrium between compound 1 and the beta-isomer of 1 (approximately 95:5) is solution is maintained under the acidic conditions, the precipitation of compound 1 from solution results in driving formation of compound 1 and lowering the beta-isomer amount. The beta isomer at the end of reaction can be controlled to less than 2.0% under these conditions. The invention also features a process for synthesis of compound 1 acetate from anidulafungin using 2,6-dimethylphenyl boronic acid as an in situ protecting agent.

The invention also features a process for synthesis of compound 1 acetate from anidulafungin using 4-trifluromethylphenyl boronic acid as an in situ protecting agent.

The invention features a purification process where the crude reaction is purified either by reverse phase preparative high performance liquid chromatography (RP-HPLC) or reverse phase preparative medium pressure liquid chromatography (RP-MPLC). The final product can be isolated by lyophilization.

The advantages of the invention include a significant improvement in diastereomeric purity, which allows for a more straightforward purification process and an overall higher purity product. Although the boronic acid group is far from the reacting center, it was surprisingly found that the nature of the groups on the aryl boronic acid had a significant impact on the diastereoselectivity in the conjugation reaction. In particular, the use of the 3,4-dimethoxyphenylboronate ester of anidulafungin reduced the amount of compound 1 beta-diastereomer formed relative to other boronate esters, resulting in a simpler purification method and higher purity of compound 1.

Compound 1 can be useful for treating, mitigating, or preventing a fungal infection or related conditions thereto in a human subject in need thereof.

Compound 1 may be prepared in a pharmaceutical composition. The pharmaceutical composition can include a salt of compound 1, or a neutral form thereof, and pharmaceutically acceptable carriers and excipients. The pharmaceutical composition can be formulated for subcutaneous injection or intravenous infusion. Depending on the mode of administration (e.g., subcutaneously or intravenously) and the dosage, compound 1 may be formulated into suitable pharmaceutical compositions to permit facile delivery. A summary of such techniques is found in Remington: The Science and Practice of Pharmacy, 22nd Edition, Lippincott Williams & Wilkins, (2012); and Encyclopedia of Pharmaceutical Technology, eds. J. Swarbrick and J. C. Boylan, 2006, Marcel Dekker, New York, each of which is incorporated herein by reference.

For subcutaneous administration, compound 1 may be formulated as an aqueous pharmaceutical composition. In some embodiments, the pharmaceutical composition containing compound 1 formulated for subcutaneous administration may not contain a buffer. In some embodiments, the pharmaceutical composition formulated for subcutaneous administration may contain a weak buffer. Examples of a weak buffer that may be used in the pharmaceutical composition include, but are not limited to, acetate, lactate, histidine, glycine, and formate.

A pharmaceutical composition including compound 1 in salt or neutral form may optionally contain an amount of a solubilizing agent. Examples of a solubilizing agent include, but are not limited to, polysorbate 20 (Tween 20; polyoxyethylene (20) sorbitan monolaurate), polysorbate 40 (Tween 40; polyoxyethylene (40) sorbitan monopalmitate), polysorbate 60 (Tween 60; polyoxyethylene (60) sorbitan monostearate), polysorbate 80 (Tween 80; polyoxyethylene (80) sorbitan monooleate), β-cyclodextrin, polyoxyl 35 castor oil (Cremophor EL), polyoxyl 40 hydrogenated castor oil (Cremophor RH 40), polyoxyl 60 hydrogenated castor oil (Cremophor RH 60), D-α-tocopheryl polyethylene glycol 1000 succinate (TPGS), sorbitan monooleate (Span 20), polyoxyl 8 stearate (PEG 400 monosterate), polyoxyl 40 stearate (PEG 1750 monosterate), PEG 400 caprylic/capric glycerides (Labrasol), PEG 300 oleic glycerides (Labrafil M-1944CS), phosphatidylcholine (lecithin), alkylglucoside, sucrose monolaurate, sucrose monooleate, and polyoxyethylene-polyoxypropylene block copolymer (Poloxamer).

Furthermore, a pharmaceutical composition including compound 1 in salt or neutral form may contain between 0.5% to 3% (w/w) of a saccharide. Examples of a saccharide that may be included in the pharmaceutical composition including compound 1 in salt or neutral form used in the methods of the invention include, but are not limited to, mannitol, sucrose, trehalose, fructose, glucose, dextrose, dextran, lactose, and sorbital.

A pharmaceutical composition including compound 1 in salt or neutral form may be formulated as a lyophilized composition. Moreover, the lyophilized composition including compound 1, when re-constituted in water for injection, may have a pH of between 5 and 6.5 (e.g., about 5, about 5.3, about 5.6, about 5.9, about 6.2, or about 6.5). In some embodiments, compound 1 in salt form may be compound 1 acetate.

The pharmaceutical compositions used in methods of the invention may be formulated in the form of liquid solutions or suspensions or lyophilized cakes and administered by a parenteral route (e.g., subcutaneous or intravenous). Pharmaceutical compositions for parenteral administration can be formulated using a sterile solution or any pharmaceutically acceptable liquid as a vehicle. Pharmaceutically acceptable vehicles include, but are not limited to, sterile water, physiological saline, or cell culture media (e.g., Dulbecco's Modified Eagle Medium (DMEM), α-Modified Eagles Medium (α-MEM), F-12 medium). Formulation methods are known in the art, see e.g., Gibson (ed.) Pharmaceutical Preformulation and Formulation (2nd ed.) Taylor & Francis Group, CRC Press (2009).

Furthermore, acceptable carriers and excipients in the pharmaceutical composition used in methods of the invention are nontoxic to recipients at the dosages and concentrations employed. Acceptable carriers and excipients may include buffers such as phosphate, citrate, histidine, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. The compositions may be formulated according to conventional pharmaceutical practice. The concentration of the compound in the formulation will vary depending upon a number of factors, including the dosage of the drug to be administered, and the route of administration.

The pharmaceutical compositions of the invention can be administered to human subjects in therapeutically effective amounts. The preferred dosage of drug to be administered is likely to depend on such variables as the type and extent of the disorder, the overall health status of the particular human subject, the specific compound being administered, the excipients used to formulate the compound, and its route of administration.

The timing of the administration of the pharmaceutical composition containing compound 1 in salt or neutral form depends on the medical and health status of the human subject. In some instances, the human subject is at risk for developing a fungal infection or a related condition and receives one or more doses treatment with compound 1 before developing symptoms or signs of a fungal infection. In some instances, the human subject has already developed a fungal infection or a related condition and receives one or more doses treatment with compound 1. The timing of the administration of the dose(s) of compound 1 may be optimized by a physician to reduce the risk of or to treat a fungal infection in a human subject.

The following examples, as set forth below, are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLES

Example 1. Synthesis of Compound 1 from the phenylboronate Ester of Anidulafungin Anidulafungin phenylboronate ester:
To a solution of anidulafungin (5 g) in tetrahydrofuran (70 mL) was added a solution of phenylboronic acid (0.7 g) in tetrahydrofuran (30 mL). The reaction mixture was stirred at room temperature for 90 minutes. The reaction mixture was concentrated by rotary evaporation. The resulting solid was dissolved in tetrahydrofuran (60 mL) and concentrated by rotary evaporation. The resulting solid was again dissolved in tetrahydrofuran (60 mL) and concentrated by rotary evaporation. The resulting solid mixture was re-dissolved in acetonitrile/tetrahydrofuran (30 mL/15 mL) and concentrated by rotary evaporation. The resulting anidulafungin phenylboronate ester solid was dried in vacuum overnight.

Choline Chloride Drying:
In a round bottom flask choline chloride (18.6 g) was suspended in acetonitrile (150 mL) and stirred for 4 hours. The suspension was concentrated by rotary evaporation. The choline chloride was suspended in acetonitrile (150 mL) and concentrated by rotary evaporation, and this step was repeated one more time. The resulting solid was dried overnight in vacuum.

Conjugation:
In a round bottom flask, the dried choline chloride was dissolved in acetonitrile (50 mL) and trifluoroacetic acid (TFA) (12.5 mL). The resulting choline chloride solution was added to the dried anidulafungin phenylboronate ester. The resulting reaction mixture was stirred at room temperature for 2.5 hours. The reaction was quenched by the addition of water (125 mL) and was basified with $NH_4OH$ (2N, ~40 mL) to pH ~2. A white material was formed and was dissolved with acetonitrile (300 mL). The material contained 4.55% compound 1 beta-diastereomer (average of two runs).

Purification:
The material was purified by preparative reversed-phase HPLC with C18 silica media using Buffer A (0.1% TFA in water) and Buffer B (0.1% TFA in 50% acetonitrile/50% water). The product was eluted using a 90 minute gradient starting with 70% B/30% A to 100% B. Pools resulting from the final purification were lyophilized to obtain the dried final bulk drug substance (2.9 g isolated compound 1).

Example 2. Synthesis of Compound 1 from the 4-(trifluoromethyl)phenylboronate Ester of Anidulafungin The reaction was carried out on 200 mg scale similar to the process of Example 1 except for the change in boronic acid to 4-(trifluoromethy)phenylboronic acid and a reaction time of 24 hours. Results: 63% compound 1; 7.0% compound 1 beta-diastereomer.

A second conjugation experiment was performed where the 4-(trifluoromethyl)phenylboronate ester was solubilized in acetonitrile:TFA mixture initially, and then the dried choline chloride solution was added to it. After 2.5 h the reaction mixture was diluted with water:acetonitrile (70:30)

and the pH was adjusted to 2.0 by addition of ammonium hydroxide. Results: 75% compound 1; 4.8% compound 1 beta-diastereomer.

Example 3. Synthesis of Compound 1 from the 2,6-dimethylphenylboronate Ester of Anidulafungin The reaction was carried out on 200 mg scale similar to the process of Example 1 except for the change to the boronic acid to 2,6-dimethylphenylboronic acid. Results: 55% compound 1; 7.4% compound 1 beta-diastereomer.

Example 4. Synthesis of Compound 1 from the 3,4-dimethoxyphenylboronate Ester of Anidulafungin The reactions were carried out on 200 mg scale similar to the process of Example 1 except for the replacing the boronic acid to 3,4-dimethoxyphenylboronic acid. Runs 1-3 were carried out to establish reproducibility of the process. Run 4 was performed with 10 equivalents of choline chloride (rather than the 30 equivalents used in Example 1). Run 5 was performed at 40° C. (rather than at room temperature as described in Example 1). Results are provided in Table 1 below.

TABLE 1

| Run No. | Compound 1 | Beta-diastereomer |
|---|---|---|
| 1 | 88.8% | 2.6% |
| 2 | 86.4% | 3.7% |
| 3 | 86.4% | 3.0% |
| 4 | 78.8% | 3.4% |
| 5 | 88.4% | 4.0% |

The use of the 3,4-dimethoxyphenylboronate ester of anidulafungin reduced the amount of compound 1 beta-diastereomer formed relative to other boronate esters.

Example 5. Synthesis of Compound 1 from the 3,4-dimethoxyphenylboronate Ester of Anidulafungin Made from a Stoichiometric Amount of 3,4-dimethoxyphenylboronic Acid The effect of using a stoichiometric amount (1.05 eq) of 3,4-dimethoxyphenylboronic acid in the conjugation step was investigated. The reaction was performed on a 500 mg anidulafungin input and performed as previously described in Example 1 except for the replacing the boronic acid to 3,4-dimethoxyphenylboronic acid. Results are provided in Table 2 below.

TABLE 2

| Boronic acid (eq) | compound 1 | compound 1 beta-diastereomer | unreacted anidulafungin | compound 1 epimer |
|---|---|---|---|---|
| 1.3 | 89.5% | 2.5% | 5.7% | 0.5% |
| 1.05 | 89.4% | 2.0% | 4.2% | 1.3% |

We can conclude from these data that while using a stoichiometric amount of boronic acid in the process may lead to a further reduction in the fraction of compound 1 beta-diastereomer that is generated, the amount of compound 1 epimer byproduct, on the other hand, is significantly increased.

Example 6. Synthesis of Compound 1 from the 3,4-dimethoxyphenylboronate Ester of Anidulafungin Choline chloride drying:

Choline chloride (185 g) was suspended in 2-methyltetrahydrofuran (500 ml) and stirred for 1 hour at room temperature. The solvent was removed under vacuum to near-dryness then dried under vacuum at 70-75° C. for 1 hour.

Anidulafungin boronate ester preparation:

Anidulafungin (50 g), 3,4-dimethoxyphenylboronic acid (10.37 g), and tetrahydrofuran (250 ml) were charged in a 1000 mL round bottom flask. The suspension was stirred at room temperature for 1.5 hours. The solvent was removed under vacuum. The resulting solid was solubilized in 2-methyltetrahydrofuran (400 mL) and the solvent was evaporated under vacuum. This process was repeated one more time.

Conjugation:

Dried choline chloride (73.6 g), acetonitrile (200 mL) and trifluoroacetic acid (48 mL) were combined. The suspension was stirred for 10 min. In a second reactor, dried anidulafungin boronate ester (25.6 g) and dry tetrahydrofuran (150 mL) were combined and stirred at room temperature until the material was completely solubilized (30 minutes). The acidic solution of choline chloride was added to the stirred boronate ester solution over 30 minutes. The resulting suspension was stirred for 3 hours at room temperature then cooled to ≤10° C. and quenched by addition of 70/30 water:acetonitrile mixture (560 mL). The pH of the crude reaction mixture was adjusted within the 2.0-2.2 range by slow addition of chilled half-dilute ammonium hydroxide solution (typically 80-82 mL). The crude solution was diluted to a final volume of 2000 mL with 70/30 water: acetonitrile solution. The compound 1 beta-diastereomer content of the crude solution was 3.7% and the compound 1 epimer content was 0.43%.

After synthesis of the crude mixture, compound 1 was purified using a reversed phase C18 silica media, with the product eluted from the column using an aqueous acetonitrile gradient. A formal acetate exchange and removal of boronic acid was performed in the same process. Final pools of the appropriate purity were brought forward to an on-column concentration using the same media to generate a concentrated solution. Post concentration, compound 1 solution was concentrated via acetonitrile removal under reduced pressure; the concentrated solution was filtered through a 0.2 μm filter and freeze-dried to produce compound 1 acetate as a white solid with 97.7% purity, 1.6% compound 1 beta-diastereomer, and 0.43% compound 1 epimer.

Example 7. Synthesis of Compound 1 from the 3,4-dimethoxyphenylboronate Ester of Anidulafungin—Effect of Dilution with Acetonitrile The boronate ester was prepared and coupled with choline chloride in acetonitrile using the conditions reported in example 6. The reaction was complete in 2-3 hours and formed a approx. 96:4 mixture of compound 1:compound 1 beta-diastereomer. This ratio was improved to >98:2 by dilution of the reaction mixture with additional acetonitrile (20-50 volumes relative to anidulafungin) at the end of the reaction, which precipitates the alpha isomer and results in conversion of beta to alpha isomer. The reaction was then quenched with aqueous ammonia/ammonium acetate to pH 4. The crude yield of compound 1 trifluoroacetate was 75-80%.

Example 8. Synthesis of Compound 1 from the 3,4-dimethoxyphenylboronate Ester of Anidulafungin—Combination of TFAA and Dilution with Acetonitrile Boronate ester slurry synthesis:

To a 1000 mL reactor the following were charged: tetrahydrofuran (250 mL), anidulafungin (25 g), 3,4-dimethoxyphenylboronic acid (5.25 g). The suspension was stirred for 1 h at room temperature. The jacket temperature was set to 30-35° C., a vacuum applied, and tetrahydrofuran distillation was initiated. Portion wise (62.5 mL) additions of tetrahydrofuran were made to maintain a constant volume in the reactor while distilling. A total of 1250 mL of tetrahydrofuran was distilled. Then, acetonitrile (500 mL) was charged and distilling re-initiated. Approximately 600 mL of tetrahydrofuran/acetonitrile mixture were distilled. Additional acetonitrile (250 mL) was charged and 250 mL of acetonitrile/tetrahydrofuran mixture distilled under vacuum. The reactor contents were cooled to 18-22° C.

Acidic choline chloride solution makeup:

Acetonitrile (57.5 mL), choline chloride (52.5 g), trifluoroacetic acid (32.5 mL) and trifluoroacetic anhydride (2.0 mL) were charged to a 250 mL round-bottom flask. The mixture was stirred at 18-22° C. for one hour.

Conjugation:

The acidic choline chloride solution was transferred to the reactor containing the slurry of boronate ester. After 1.75 to 2.00 hours post mixing, acetonitrile (285 mL) was added to the reaction mixture and stirred at 10-15° C. for 1 hour. Additional acetonitrile (285 mL) was then added. If the % compound 1 beta-diastereomer was >2.0%, additional acetonitrile (142 mL) was added. After 0.5 hours, the reaction was quenched by adding chilled ammonium acetate solution (143 mL) followed by slow addition of a chilled solution of 9M aqueous ammonium hydroxide (28.7 mL) so as to maintain a temperature <15° C. and bring the pH within a range of 4.0-4.7. The crude yield of compound 1 trifluoroacetate was 75-80% with less than 2% compound 1 beta-diastereomer.

Example 9. Synthesis of Compound 1 from the 3,4-dimethoxyphenylboronate Ester of Anidulafungin—Coupling in the Presence of TFAA Tetrahydrofuran (700 mL) and anidulafungin (108.44 g) were charged to a 1 L reactor. 3,4-Dimethoxyphenylboronic acid (21.0 g) was then charged and the mixture was stirred at 18-22° C. The reaction mixture was azeodried by distillation of tetrahydrofuran and simultaneous addition of fresh tetrahydrofuran (7.0 L). A constant volume solvent swap to acetonitrile was carried out by addition of acetonitrile (2.1 L) and simultaneous vacuum distillation. After complete turnover to acetonitrile, further distillation was carried out to reduce the volume to 420 mL.

In a separate vessel, the following were combined with stirring: choline chloride (172 g), acetonitrile (217 mL), trifluoroacetic acid (142 mL), and trifluoroacetic anhydride (8.6 mL). This solution was then added to the slurry containing the anidulafungin boronate ester and the resulting mixture was stirred at 15° C. for 8 hours. The reaction was quenched by charging cooled (T<10° C.) solution of ammonium acetate (4.2 M, 221 mL) to the reactor at once followed by addition of chilled (T<10° C.)) water (221 mL). Then, a cooled (10° C.) solution of ammonium hydroxide (9.0 M, 126.4 mL) was added. The final pH was adjusted to pH 4.0-4.6 by addition of ammonium hydroxide. The crude reaction mixture was diluted with water:acetonitrile (3:1, 6 L) and stored at −20° C.

Results: compound 1, 76.8%, compound 1 beta-diastereomer, 0.8%.

A reduction in the level of compound 1 beta-diastereomer has allowed for replacement of the HPLC purification with medium pressure chromatography (MPLC) using a coarser grade of C18 silica (25 to 50 μm). The 3,4-dimethoxyphenyl boronic acid can be separated by ion-exchange capture, eluting with 100 mM ammonium acetate (pH 4.5) in water:acetonitrile 50:50 v:v, which affords salt exchange from trifluoroacetate to acetate.

Post chromatography, the compound 1 acetate solution was concentrated by vacuum distillation to remove the majority of acetonitrile. The concentrated solution was filtered through a 0.2 μm filter and freeze-dried to produce compound 1 acetate. The purity after MPLC and after ion exchange and lyophilization is provided in Table 3 below.

TABLE 3

| Stage | compound 1 | compound 1 beta-diastereomer | compound 1 epimer |
|---|---|---|---|
| after MPLC | 98.47% | 0.77% | 0.47% |
| after ion exchange and lyophilization | 98.49% | 0.77% | 0.51% |

Other Embodiments

All publications, patents, and patent applications mentioned in this specification are herein incorporated by reference to the same extent as if each independent publication or patent application was specifically and individually indicated to be incorporated by reference.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure that come within known or customary practice within the art to which the disclosure pertains and may be applied to the essential features hereinbefore set forth, and follows in the scope of the claims. Other embodiments are within the claims.

What is claimed is:

1. A method of synthesizing compound 1:

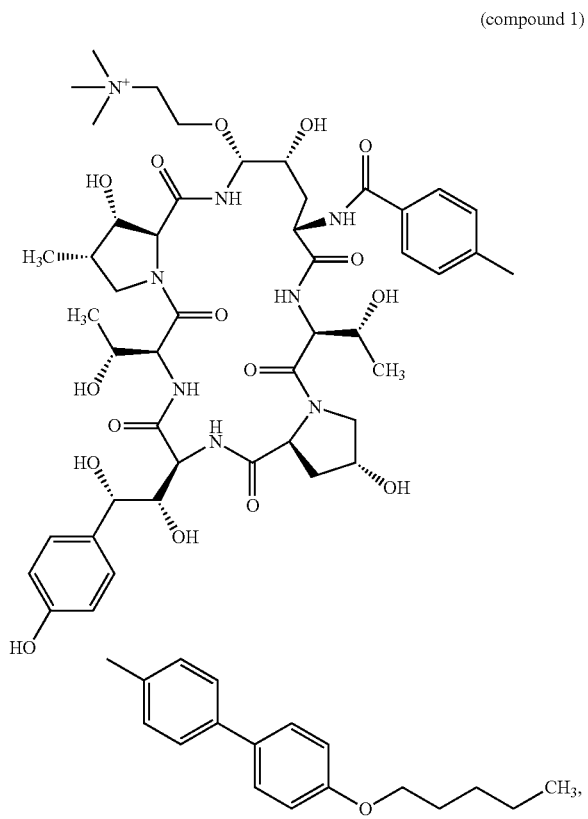

(compound 1)

said method comprising:
(a) providing a first composition comprising a boronate ester of anidulafungin;
(b) providing a second composition comprising a salt of choline;
(c) combining the first composition, the second composition, and trifluoroacetic acid in a solvent system that comprises acetonitrile and trifluoroacetic anhydride to form a precipitate of a reaction product having formula (I):

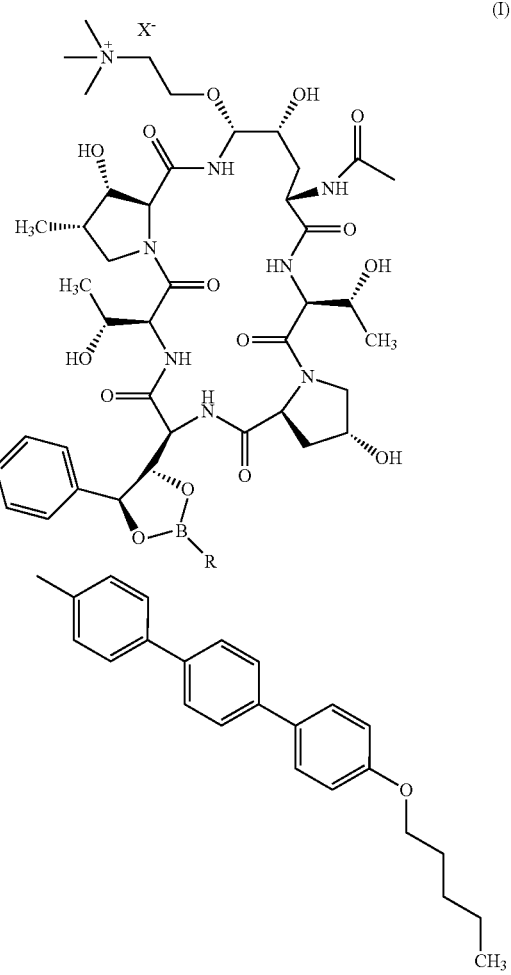

wherein
$X^-$ is an anion; and
R is $C_1$-$C_6$ alkyl or $C_6$-$C_{10}$ aryl;
and;
(d) hydrolyzing the compound of formula (I) to form compound 1, or a salt or neutral form thereof.

2. The method of claim 1, wherein the concentration of the mixture is at least 0.01 moles per L relative to the compound of formula (I).

3. The method of claim 1, wherein step (c) comprises forming a mixture in a solvent system comprising a mixture of tetrahydrofuran and acetonitrile.

4. The method of claim 1, wherein step (c) comprises forming a mixture comprising at least 10 molar equivalents of the salt of choline and at least 1 molar equivalents of the boronate ester of anidulafungin.

5. The method of claim 1, wherein step (c) is performed at a temperature of less than 40° C.

6. The method of claim 1, wherein step (c) comprises forming a mixture in which at least 50% of the compound of formula (I) is precipitated.

7. The method of claim 1, wherein R is $C_6$-$C_{10}$ aryl.

8. The method of claim 1, wherein R is $C_1$-$C_6$ alkyl.

9. A method of synthesizing compound 1:

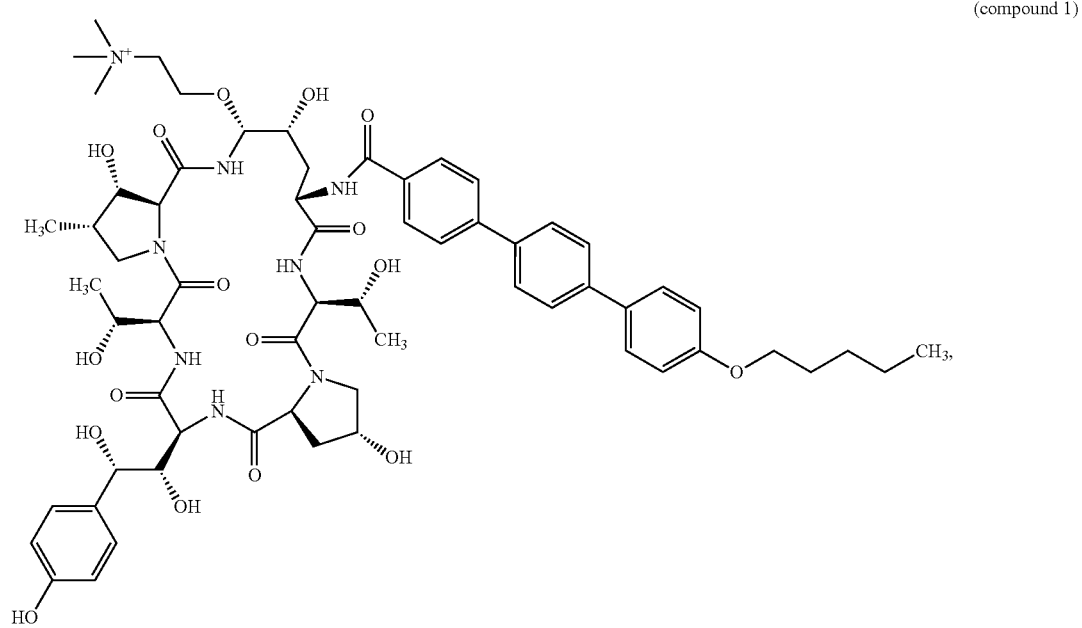 [SMILES: CCCCCOc1ccc(-c2ccc(-c3ccc(C(=O)N[C@H]4C[C@@H](O)[C@@H](OCC[N+](C)(C)C)NC(=O)[C@@H]5[C@@H](O)[C@@H](C)CN5C(=O)[C@H]([C@@H](C)O)NC(=O)[C@H]([C@H](O)[C@@H](O)c5ccc(O)cc5)NC(=O)[C@@H]5C[C@@H](O)CN5C(=O)[C@H]([C@@H](C)O)NC4=O)cc3)cc2)cc1]
(compound 1)

said method comprising:
(a) providing a first composition comprising an aryl boronate ester of anidulafungin;
(b) providing a second composition comprising a salt of choline;
(c) combining the first composition, the second composition, and an acid to form a mixture comprising a compound of formula (II):

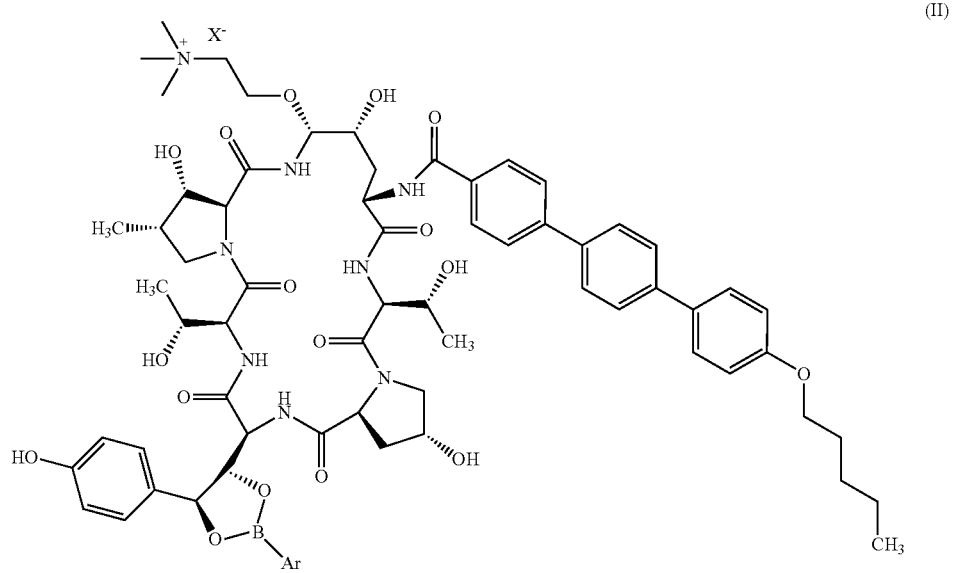
(II)

wherein
X⁻ is an anion; and
Ar is substituted $C_6$ aryl; and
(d) hydrolyzing the compound of formula (II) to form compound 1, or salt or neutral form thereof.

10. The method of claim 9, wherein Ar is selected from 3,4-dimethoxyphenyl, 2,6-dimethylphenyl, and 4-trifluoromethylphenyl.

11. The method of claim 9, wherein step (c) comprises combining at least 10 molar equivalents of the salt of choline with at least 1 molar equivalents of the boronate ester of anidulafungin.

12. The method of claim 9, wherein the first composition comprises a solution of the boronate ester of anidulafungin dissolved in an organic solvent selected from acetonitrile, butyronitrile, tetrahydrofuran, or 2-methyltetrahydrofuran, or a mixture thereof.

13. The method of claim 9, wherein the second composition comprises a solution of the salt of choline dissolved in a mixture of acetonitrile and trifluoroacetic acid.

14. The method of claim 9, wherein the second composition comprises a solution of the salt of choline dissolved in a mixture of acetonitrile, trifluoroacetic acid, and trifluoroacetic anhydride.

15. The method of claim 9, wherein step (c) further comprises adding acetonitrile to the mixture to reduce the level of beta-diastereomer.

16. The method of claim 9, wherein step (d) further comprises diluting with at least 5 volumes relative to anidulafungin of water:acetonitrile mixture of about 80:20 to 50:50 and adjusting the pH with base to a pH of from 2 to 5.

17. The method of claim 9, wherein step (d) comprises forming a reaction product comprising greater than 70% compound 1 and less than 4% compound 1 beta-diastereomer.

18. The method of claim 9, wherein the hydrolyzing is performed at a temperature of less than 15° C.

19. The method of claim 9, wherein the method further comprises producing a pharmaceutical composition by combining the compound 1 with a pharmaceutically acceptable excipient.

20. The method of claim 9, wherein the acid of step (c) is trifluoroacetic acid.

21. The method of claim 9, wherein the solvent system of step (c) comprises acetonitrile and trifluoroacetic anhydride.

22. The method of claim 9, wherein the method further comprises the step (e) purifying compound 1, or a salt or neutral form thereof, by reverse phase preparative high performance liquid chromatography or reverse phase preparative medium pressure liquid chromatography.

23. The method of claim 1, wherein the method further comprises step (e) purifying compound 1, or a salt or neutral form thereof, by reverse phase preparative high performance liquid chromatography or reverse phase preparative medium pressure liquid chromatography.

* * * * *